United States Patent
Pastore et al.

(10) Patent No.: US 6,829,506 B2
(45) Date of Patent: Dec. 7, 2004

(54) LINEAR STIMULATION OF THE HEART FOR IMPROVED HEMODYNAMIC BENEFIT

(75) Inventors: Joseph M. Pastore, Minneapolis, MN (US); Qingsheng Zhu, Little Canada, MN (US); Rodney W. Salo, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 310 days.

(21) Appl. No.: 09/915,088

(22) Filed: Jul. 25, 2001

(65) Prior Publication Data

US 2003/0023278 A1 Jan. 30, 2003

(51) Int. Cl.$^7$ ............................................... A61N 1/362
(52) U.S. Cl. ............................................................. 607/9
(58) Field of Search ............................ 607/4, 5, 9, 129

(56) References Cited

U.S. PATENT DOCUMENTS

| | | | |
|---|---|---|---|
| 5,165,403 A | 11/1992 | Mehra | |
| 5,174,288 A | 12/1992 | Bardy et al. | |
| 5,417,717 A | 5/1995 | Salo et al. | |
| 5,540,727 A | 7/1996 | Tockman et al. | |
| 5,603,732 A | * 2/1997 | Dahl et al. | 607/129 |
| 5,643,328 A | 7/1997 | Cooke et al. | |
| 5,792,203 A | 8/1998 | Schroeppel | |
| 5,824,028 A | 10/1998 | Knisley | |
| 5,849,033 A | * 12/1998 | Mehmanesh et al. | 607/129 |
| 5,897,586 A | * 4/1999 | Molina | 607/129 |
| 5,902,236 A | 5/1999 | Iversen | |
| 5,919,222 A | 7/1999 | Hjelle et al. | |

* cited by examiner

Primary Examiner—Jeffrey R. Jastrzab
(74) Attorney, Agent, or Firm—Merchant & Gould P.C.

(57) ABSTRACT

A method and apparatus for linear stimulation of the heart to resynchronize contraction for improved hemodynamic benefit. Linear stimulation may be accomplished using a linear source, which may comprise an elongated electrode or plurality of electrodes arranged so as to linearly stimulate the heart. A linear source may be coupled to the left ventricle, and one or more additional electrodes may be positioned so as to stimulate a separate region of the left ventricle or one or more additional chambers of the heart as well. Application of an electrical stimulus by the linear source may function to stimulate a larger region of the heart, thereby enhancing the resynchronization effect as well as providing other hemodynamic benefits.

9 Claims, 8 Drawing Sheets

LINEAR STIMULATION OF THE HEART FOR IMPROVED HEMODYNAMIC BENEFIT

TECHNICAL FIELD

This invention relates to cardiac rhythm management devices for the heart. In addition, the invention relates to linear stimulation of the heart in order to provide improved hemodynamic benefits.

BACKGROUND

A normal human heart 100, as illustrated in FIG. 1, includes a right atrium 106, a left atrium 110, a right ventricle 131, and a left ventricle 132. The ventricles 131, 132 further comprise a right ventricular free wall 133, a left ventricular free wall 134, and an interventricular septum 135 dividing the ventricles. The electrical propagation system of the heart includes a sinoatrial (SA) node 120, an atrioventricular (AV) node 122, a bundle of His 124 dividing into a right branch of bundle of His 126 and left branch 128, and a plurality of Purkinje fibers 112 dispersed throughout ventricular myocardium 136.

During normal contraction, the SA node 120 initiates the excitation of the heart 100, sending an electrical cardiac pulse through the atria and ventricles. Once initiated by the SA node 120, the cardiac pulse is transmitted through right and left atria 106,110, causing the atria to contract and pump blood from the atria to the ventricles. The cardiac pulse is then further transmitted through the AV node 122 to ventricles 131,132. Transmission in the ventricles 131,132 is accomplished using a conduction system including the bundle of His 124, which divides into the right branch 126 and left branch 128, and finally the Purkinje fibers positioned throughout the ventricular myocardium 136. The transmitted cardiac pulse causes the ventricles to contract, pushing the blood from the ventricles out into the pulmonary and systemic circulatory systems.

In patients with certain heart abnormalities, such as, for example, congestive heart failure and left bundle branch block, the electrical conduction patterns of the left ventricle 132 can be altered or impaired. These abnormalities can in turn cause the interventricular septum 135 to contract before the left ventricular free wall 134, creating asynchronous left ventricular contraction and causing impaired hemodynamic function.

Recently, it has been demonstrated that through the use of atrial synchronous ventricular pacing, the left ventricular contractions in patients with the heart abnormalities described above can be resynchronized. Resynchronization differs from typical pacing performed by devices such as a pacemaker in that the goal of resynchronization is not to alter the rate at which the heart is contracting, but instead to alter the manner in which the contraction occurs. Resynchronization is a process that can involve the application of an electrical stimulus to the left ventricle or both the left and right ventricles after pacing has been detected in the atria. This electrical stimulus forces the septum 135 and free wall 134 to contract at approximately the same time, thereby resynchronizing left ventricular contraction. This resynchronization provides both acute and chronic hemodynamic benefits.

At present, resynchronization has been implemented by resynchronizing the left ventricle or both ventricles using a single point source for each ventricle. An example of a prior art cardiac rhythm management (CRM) device using a single point source is shown in FIG. 2. The left ventricle 132 illustrated in FIG. 2 includes the interventricular septum 135 and interventricular free wall 134 with free wall points 236,237 noted. The resynchronization system 200 includes CRM device 201, lead 203, and single point source 205. The single point source 205 is typically coupled via the lead 203 to the CRM device 201, with the CRM device 201 providing the electrical stimulus for resynchronization. Single point source 205 is constructed with a small surface area such that single point source 205 contacts only a small region of the surface of the left ventricular free wall 134 where point source 205 is located, such as at free wall point 237.

Electrical propagation using a single point source differs from that of the propagation of a cardiac pulse during normal sinus rhythm. In normal sinus rhythm, the bundle of His 124 and Purkinje fibers 112 enhance conduction so that the entire ventricle is activated almost instantaneously, thereby causing the left ventricular contraction time to be very short in duration. In contrast, using a single point source, such as 205 as shown in FIG. 2, electrical propagation from the site at which the single point source contacts the surface of the left ventricle 132 at free wall point 237 to the rest of the ventricular muscle, such as free wall point 236, is much slower, prolonging the left ventricular contraction time. This prolongation of contraction time compared to normal contraction makes the ventricle less efficient.

A further limitation of resynchronization through use of a single point source is the inability to adequately alleviate local wall stress. Local wall stress is a phenomenon that occurs when the interventricular septum 135 contracts before the ventricular free wall 134, forcing the blood contained within ventricle 132 that is displaced by the septum 135 to push against and distend free wall 134. A reduction in local wall stress has been shown through use of a single point source 205, as shown in FIG. 2. However, this reduction in local wall stress is limited to the area immediately adjacent to free wall point 237, and other remote areas of the ventricular free wall, such as free wall region 236, may still exhibit local wall stress.

Therefore, although some advantage may be gained through use of a single point source to assist in resynchronization of the left ventricular free wall and interventricular septum contractions, use of a single point source may still result in a hemodynamically suboptimal situation.

SUMMARY

Generally, the present invention relates to cardiac rhythm management devices for the heart. In addition, the invention relates to linear stimulation of the heart in order to provide improved hemodynamic benefits. In one aspect of the disclosure, a method of resynchronization of a heart may comprise the steps of coupling a linear source to a cardiac rhythm management device via a lead, coupling the linear source to a surface of the heart; and resynchronizing a contraction of the heart through linear excitation of the surface by the linear source.

In another aspect, the disclosure provides another method of resynchronization of a heart comprising the steps of coupling a first linear source to a left ventricular free wall nearer an apex of the heart and sending a first electrical stimulus to the first linear source.

In still yet another aspect, the disclosure provides an apparatus to resynchronize a heart by using atrial synchronous ventricular pacing comprising a cardiac rhythm management device, linear source coupled to a portion of a ventricular myocardium surface of the heart, and a lead coupled at a first lead end to the cardiac rhythm management device and at a second lead end to the linear source.

In still yet another aspect, the disclosure further provides an apparatus to resynchronize a heart comprising first means for providing an electrical stimulus to stimulate the heart, second means for exciting a linear region of a surface of the left ventricle, and means for electrically coupling the first means to the second means.

In still yet another aspect, the disclosure provides an apparatus to resynchronize contraction of a left ventricular free wall of a heart using atrial synchronous ventricular pacing, the apparatus comprising a cardiac rhythm management device for creating an electrical stimulus, a lead coupled to the cardiac rhythm management device at a first lead end, and a linear source coupled to the lead at a second lead end. Further in this aspect, the linear source may comprise a contact surface coupled to the left ventricular free wall at a free wall region, wherein the contact surface spans in a linear direction and wherein the contact surface transmits the electrical stimulus so as to linearly excite the free wall region along the entire contact surface and thereby promote resynchronization of contraction of the left ventricular free wall.

The above summary of the present invention is not intended to describe each disclosed embodiment or every implementation of the present invention. The figures and the detailed description that follow more particularly exemplify these embodiments.

DESCRIPTION OF THE DRAWINGS

The invention may be more completely understood in consideration of the following detailed description of various embodiments of the invention in connection with the accompanying drawings, in which.

Figure 1:
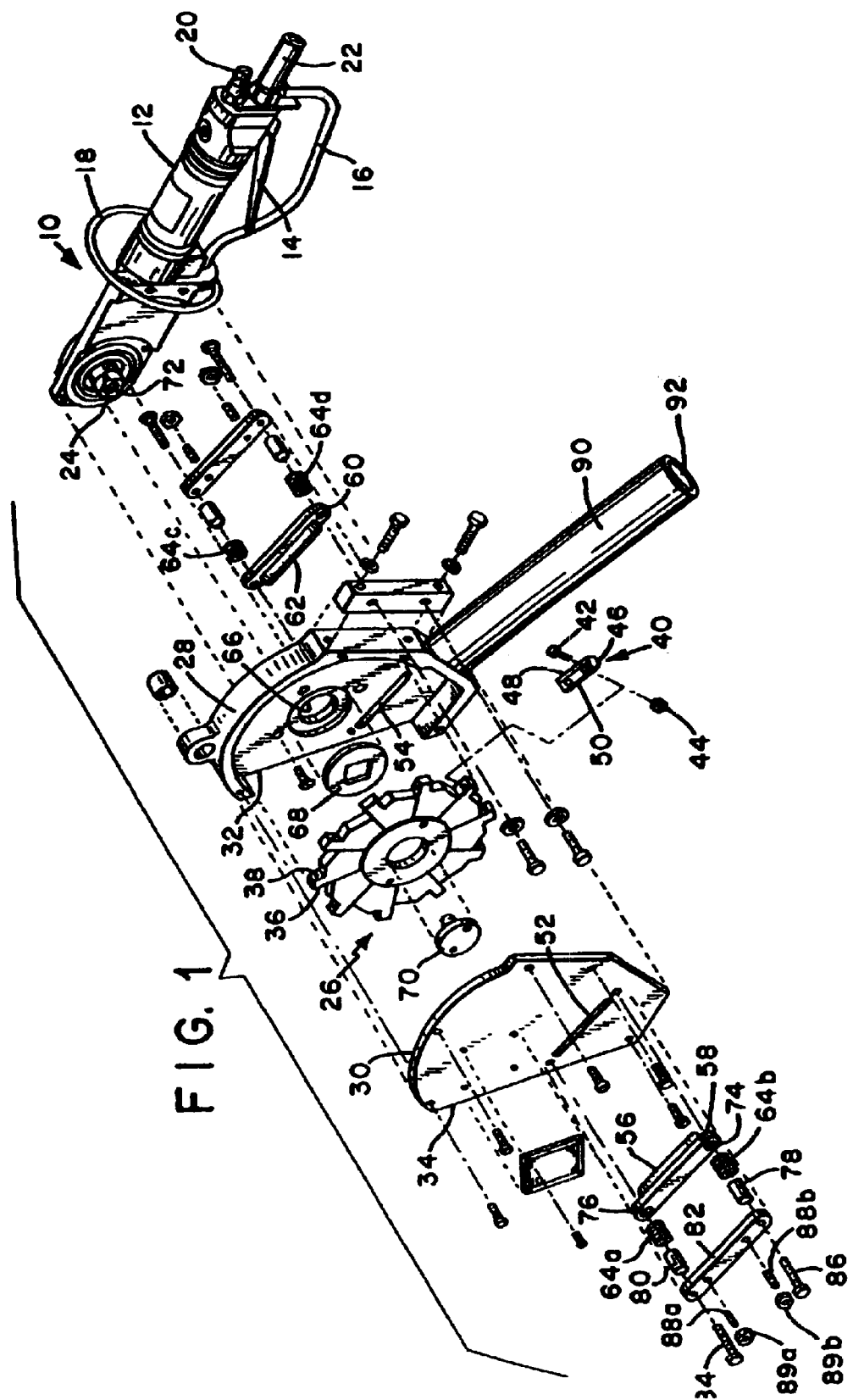
FIG. 1 illustrates the anatomical structures of a typical heart.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be applicable to cardiac rhythm management (CRM) devices for the heart. In particular, the present invention is directed to linear stimulation of the heart in order to provide improved hemodynamic benefits. While the present invention is not so limited, an appreciation of various aspects of the invention will be gained through a discussion of the examples provided below.

Linear stimulation is herein defined as any form of electrical stimulation provided to a target area, where the target area is larger than the area that may be stimulated using a point source. Linear stimulation of the heart may be accomplished using, for example, a linear source. A linear source is herein defined as one or more electrodes or other such devices that are adapted to linearly stimulate an area of the heart. The linear source may comprise a single, elongated electrode as well as a plurality of smaller electrodes positioned so as to cause linear simulation. One skilled in the art will understand that other embodiments for a linear source are also possible. An application in which a linear source may be used is in resynchronization of the contraction of the heart.

Figure 3:
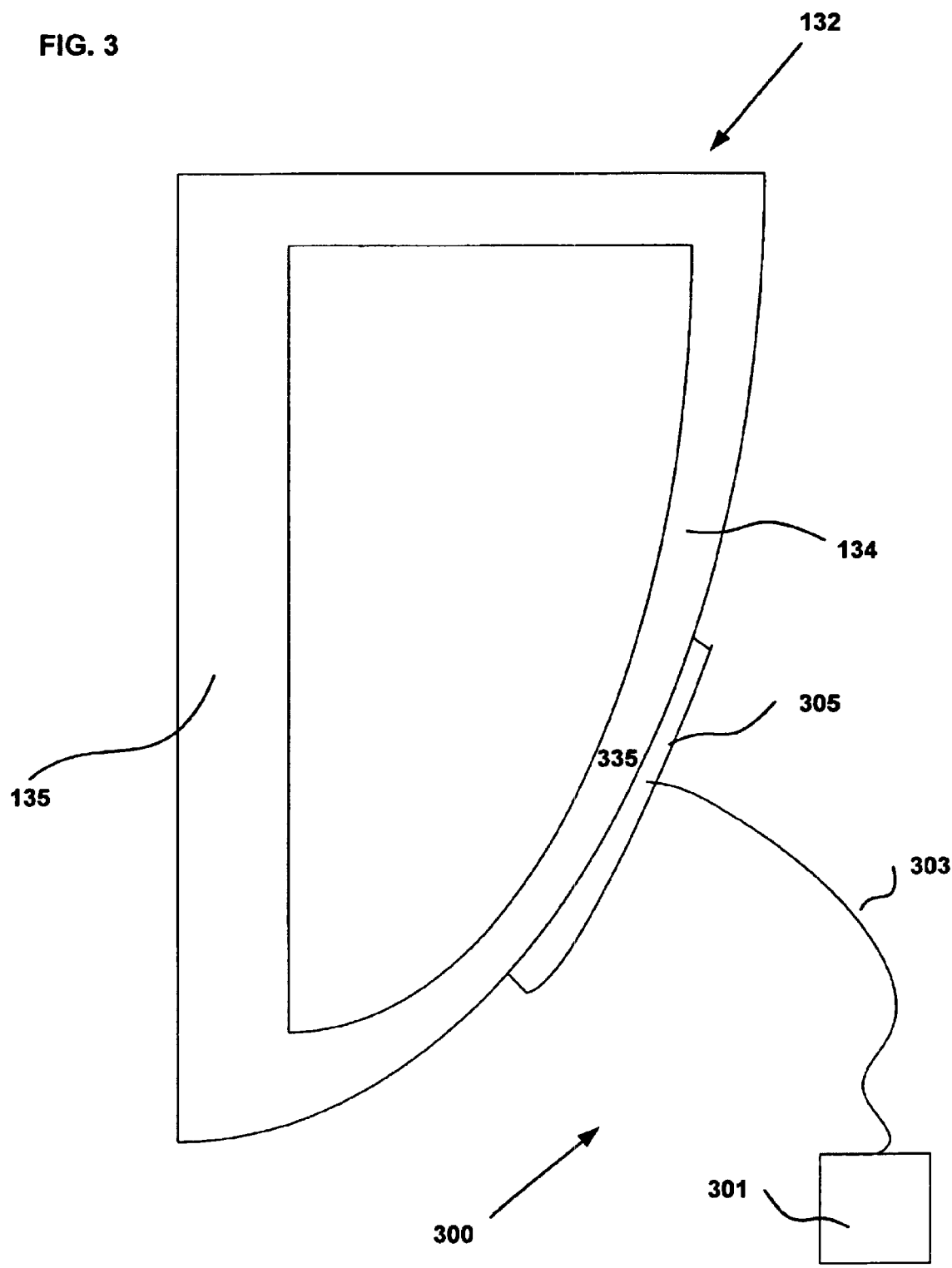
FIG. 3 illustrates a linear source resynchronization system implemented according to a preferred embodiment of the present invention.

Referring now to FIG. 3, the left ventricle 132 is illustrated including interventricular septum 135 and left ventricular free wall 134 with free wall region 335 noted. Also included is resynchronization system 300 comprising CRM device 301, lead 303, and linear source 305.

Examining resynchronization system 300, the CRM device 301 may consist of any device that can generate and communicate an electrical stimulus to the heart so as to resynchronize it. One example of such a CRM device would be a pacemaker. Other devices may also be used that can provide an electrical stimulus to initiate contraction of the heart.

The CRM device 301 of resynchronization system 300 may be coupled to the linear source 305 via lead 303. Lead 303 may consist of any material adapted to conduct an electrical stimulus from the CRM device 301 to the linear source 305. The linear source 305 is positioned so as to contact free wall region 335 of the left ventricular free wall 134.

Figure 4:
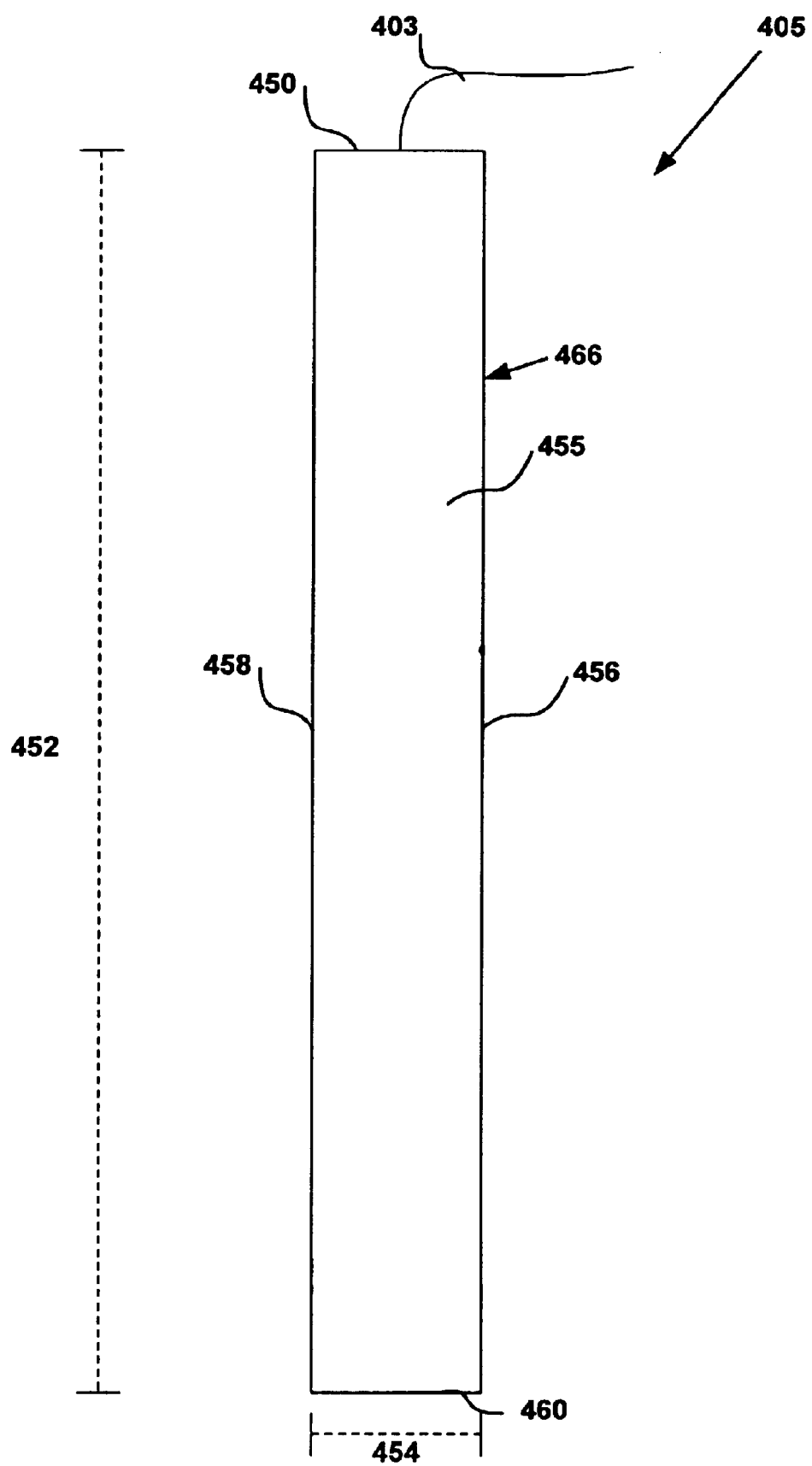
FIG. 4 is a top view of a linear source implemented as a single, long electrode, according to a preferred embodiment of the present invention.

Two preferred embodiments of a linear source according to the invention are shown in more detail in FIGS. 4 and 5. In FIG. 4, the linear source 405 comprises elongated linear body 466 including first end 450, second end 460, sidewalls 456,458, contact surface 455, and dimensions 452 and 454. A lead 403 is also shown. The distance 452 between ends 450 and 460, or the length of linear source 405, may be preferably larger than a single point source as described above and illustrated as 205 in FIG. 2.

As shown in FIG. 4, sidewalls 456 and 458 are illustrated so as to be generally parallel to one another to create a generally linear body 466. However, it should be understood that the linear source 405 need not consist of a body 466 with substantially parallel sidewalls, but may instead consist of a body that is curved or otherwise not strictly linear so long as contact surface 455 may contact a significant linear portion of the ventricular free wall.

Figures 5A, 5B:
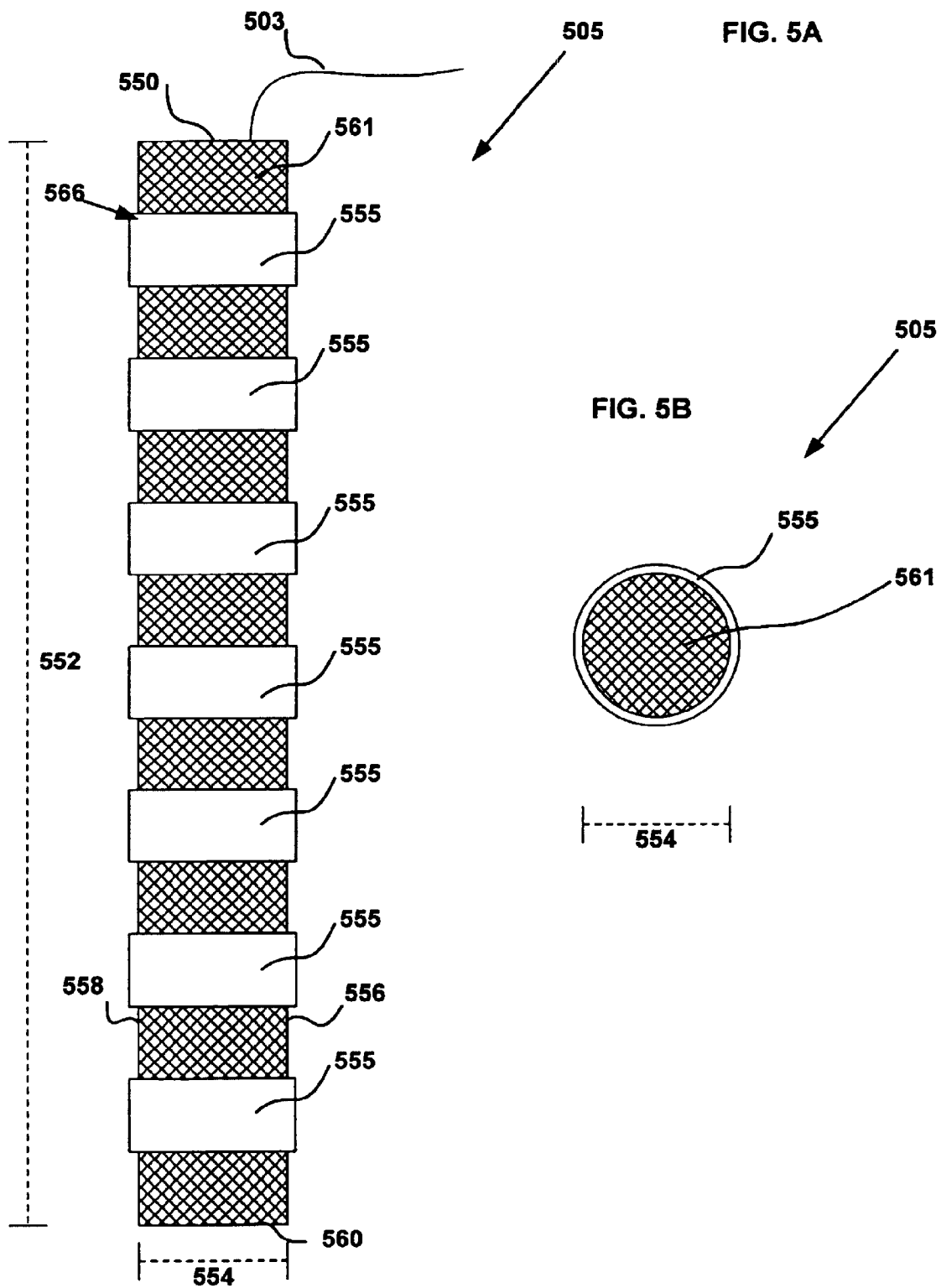
FIGS. 5A and 5B are top and front views, respectively, of a linear source implemented as multiple, closely spaced electrodes, according to another preferred embodiment of the present invention.

Another preferred embodiment for a linear source according to the invention is shown in FIGS. 5A–5B. FIG. 5A consists of a top plan view of linear source 505 comprising elongated linear body 566 including first end 550, second end 560, sidewalls 556,558, contact surfaces 555, dielectric base 561, and dimensions 552 and 554. One or more leads 503 are also shown. The linear body 566 in this embodiment may consist of the dielectric base 561 with a plurality of contact surfaces 555 disposed thereon. The number of contact surfaces 555 may vary, as can the length 552 and width 554 of the linear source 505.

FIG. 5B is a front view of the linear source 505. As shown, the dielectric base 561 may be positioned in the center, with the plurality of contact surfaces 555 positioned in a cylindrical arrangement around the dielectric base 561. In this manner, the contact surfaces 555 are positioned so that they may contact a surface of the heart when placed in close proximity.

Electrical stimuli may be sent to each of the plurality of contact surfaces 555 of linear source 505 at the same time. Further, an electrical stimulus may be sent to each adjacent contact surface 555 after a predetermined delay, or an electrical stimulus may be sent to one or more contact surfaces based on a predetermined pattern. Multiple leads 503 may be used if independent control of each contact surface 555 is desired. In this manner, the plurality of contact surfaces 555 may be utilized to approximate a waveform based on the delay between stimulation of the different contact surfaces. A CRM device or other logic circuit may control when and how each electrical stimulus is sent to each of the plurality of contact surfaces.

In these exemplary embodiments according to the invention, the dimensions 454,554 for linear sources 405 and 505 may be approximately 1.5 mm to 3 mm and dimensions 452,552 may be approximately 2–5 cm. In other embodiments, the dimensions 452,552 may be less than 6 cm. One skilled in the art should understand that the dimensions provided are by way of example only and that other dimensions may also be used so as to maximize the hemodynamic benefits associated with resynchronization therapy.

The contact surfaces 455,555 of linear sources 405 and 505 may be constructed of any material that is suitable for conduction of the electrical stimulus from the leads 403,503 to a surface of the heart. In accordance with the example embodiments of the invention, the materials used to construct the contact surfaces 455,555 may be an alloy comprising platinum and iridium. The dielectric base 561 of linear source 505 may be constructed of any typical dielectrical material that restricts the conduction of electrical current such as, in this exemplary embodiment, silicone and polyurethane. It should be understood that the materials listed are by way of example only and that other materials that perform similar functions may also be used without departing from the scope of the invention.

The embodiments shown in FIGS. 4 and 5A–5B are by way of example only, and other configurations could be used to implement a linear source without departing from the scope of the invention. The embodiments shown merely illustrate examples of possible linear source configurations with one or more contact surfaces that may provide linear stimulation, as described below, to a surface of the heart.

Referring back to FIG. 3, the resynchronization system 300 may function to resynchronize the left ventricular contraction of the heart. During normal cardiac performance, the interventricular septum 135 and the left ventricular free wall 134 will contract almost simultaneously, thereby effectively forcing blood from the left ventricle into the pulmonary system. However, as described above, in an individual with electrical conductive path abnormalities, the interventricular septum 135 will typically contract before the left ventricular free wall 134, causing a decrease in hemodynamic efficiency.

In resynchronization system 300, the linear source 305 is surgically positioned so as to be in direct contact with the left ventricular free wall 134 at free wall region 335. Resynchronization of the ventricles may be initiated after the CRM device detects atrial stimulation, either during normal sinus activity or through artificial pacing of the atria. Atrial stimulation may be detected using one or more leads coupled to the atrium (not shown). Once atrial contraction has occurred, an electrical stimulus may then be communicated by CRM device 301 through lead 303 to linear source 305. The electrical stimulus is further conducted through the linear source 305 to the left ventricular free wall 134, causing linear excitation at free wall region 335. The electrical stimulus thus provided at the left ventricular free wall 134 may cause the free wall 134 to contract, and by timing communication of the electrical stimulus to coincide with the contraction of the interventricular septum 135, resynchronization of the left ventricle 132 contractions may thereby be achieved.

Figure 2:
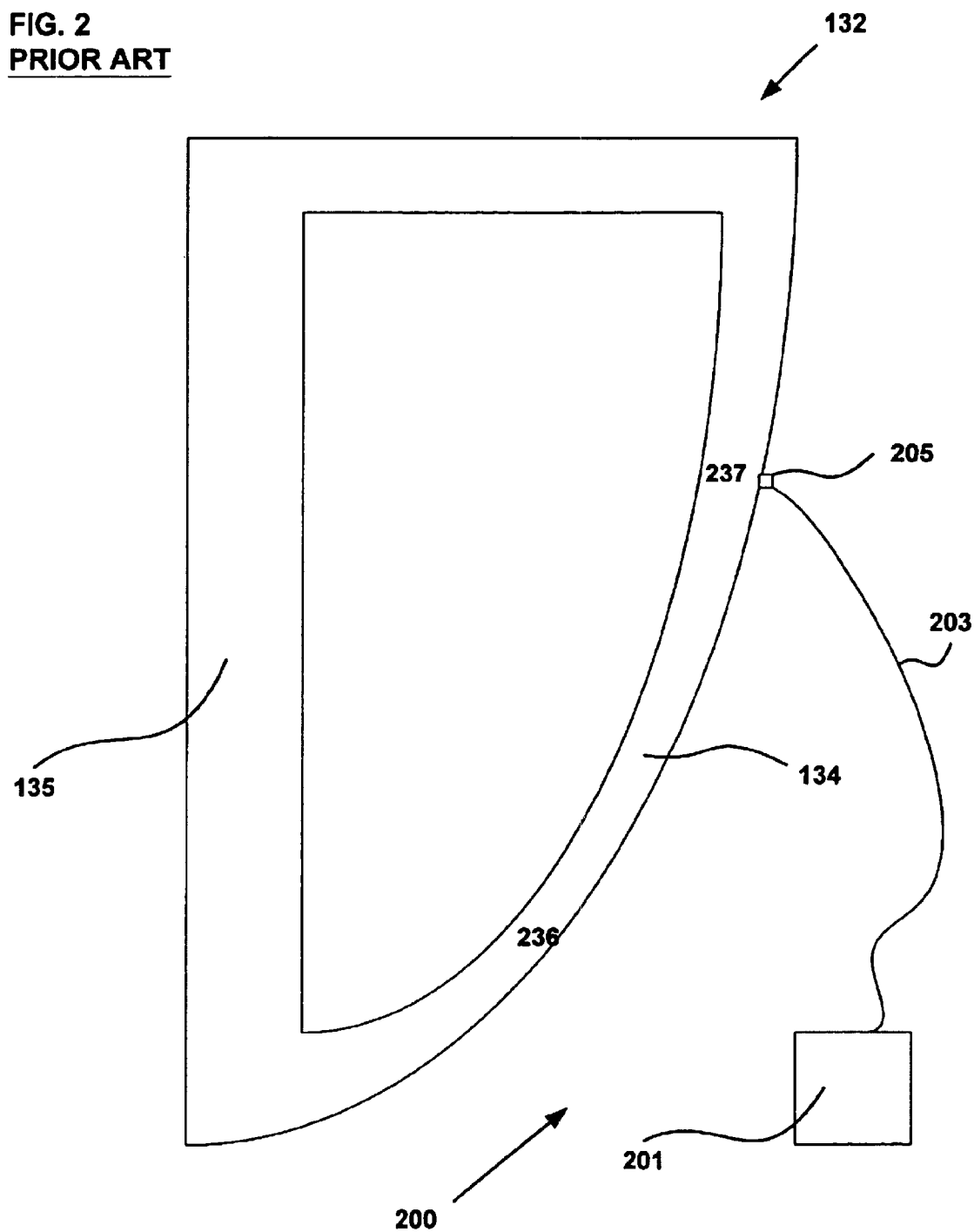
FIG. 2 depicts a prior art single point source resynchronization system.

Use of a linear source 305 such as provided in resynchronization system 300 may be more effective than use of a single point source as shown in FIG. 2 for several reasons. First, resynchronization using a linear source may activate a larger region of tissue (i.e. free wall region 335) at the time of stimulation, which could cause a larger portion of the left ventricular free wall 134 to contract simultaneously. Further, research has shown that individuals with certain conductive heart abnormalities such as left branch bundle block exhibit an area of slow conduction on the left ventricle between the septum 135 and the free wall 134. However, these individuals further exhibited an area of fast conduction on the ventricular free wall. Therefore, use of a linear source to provide linear excitation to the left ventricular free wall may result in both a larger region of tissue being activated at the time of resynchronization as well as faster propagation from the linear source to the remaining portions of the left ventricular free wall. Both of these advantages result in a closer approximation of natural contraction of the heart during normal sinus rhythm and are hemodynamically beneficial.

Second, use of a linear source for resynchronization has the further benefit of reducing local wall stress. Local wall stress due to asynchronization can be caused by dilation of the heart, which is common in individuals that have had congestive heart failure or left branch bundle block. Local wall stress is exhibited mainly at the ventricular free wall and is caused by the asynchronous contraction of the heart, as described above. Through use of linear source such as 305 shown in FIG. 3 with a surface area larger than a single point source, the area of linear excitation at free wall region 335 may be increased. Increasing the size of the region stimulated during resynchronization may reduce wall stress over a larger area, thereby increasing therapy benefit.

Figure 6:
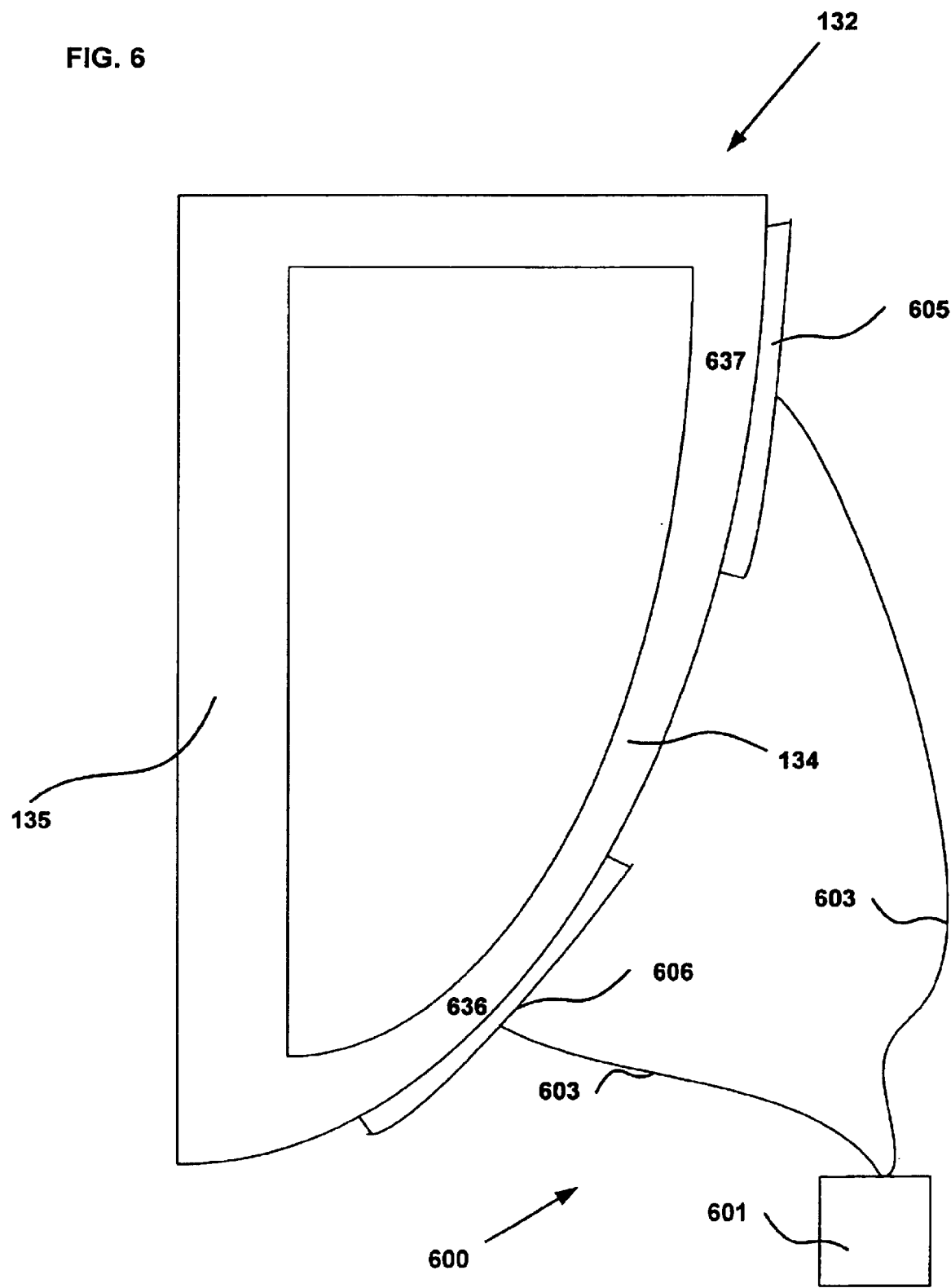
FIG. 6 illustrates a linear source resynchronization system with multiple linear sources implemented according to another preferred embodiment of the invention.

A second embodiment of a resynchronization system 600 according to the present invention is illustrated in FIG. 6. The left ventricle 132 is shown with interventricular septum 135 and left ventricular free wall 134 with free wall regions 636,637 noted. The resynchronization system 600 includes CRM device 601, leads 603, first linear source 605, and second linear source 606.

The resynchronization system 600 functions in a similar manner to that of system 300 shown in FIG. 3, except that system 600 includes dual linear sources 605 and 606. Linear source 605 can be positioned near the base of the heart at free wall region 637, while linear source 606 may be placed near the apex of the heart at free wall region 636. Once in place, an electrical stimulus may be sent by CRM device 601 to both sources 605,606 at the same time, effectively treating the linear sources as a single unit. Or, CRM device 601 may separately control each linear source and communicate an electrical stimulus to one or the other independently.

Figure 7:
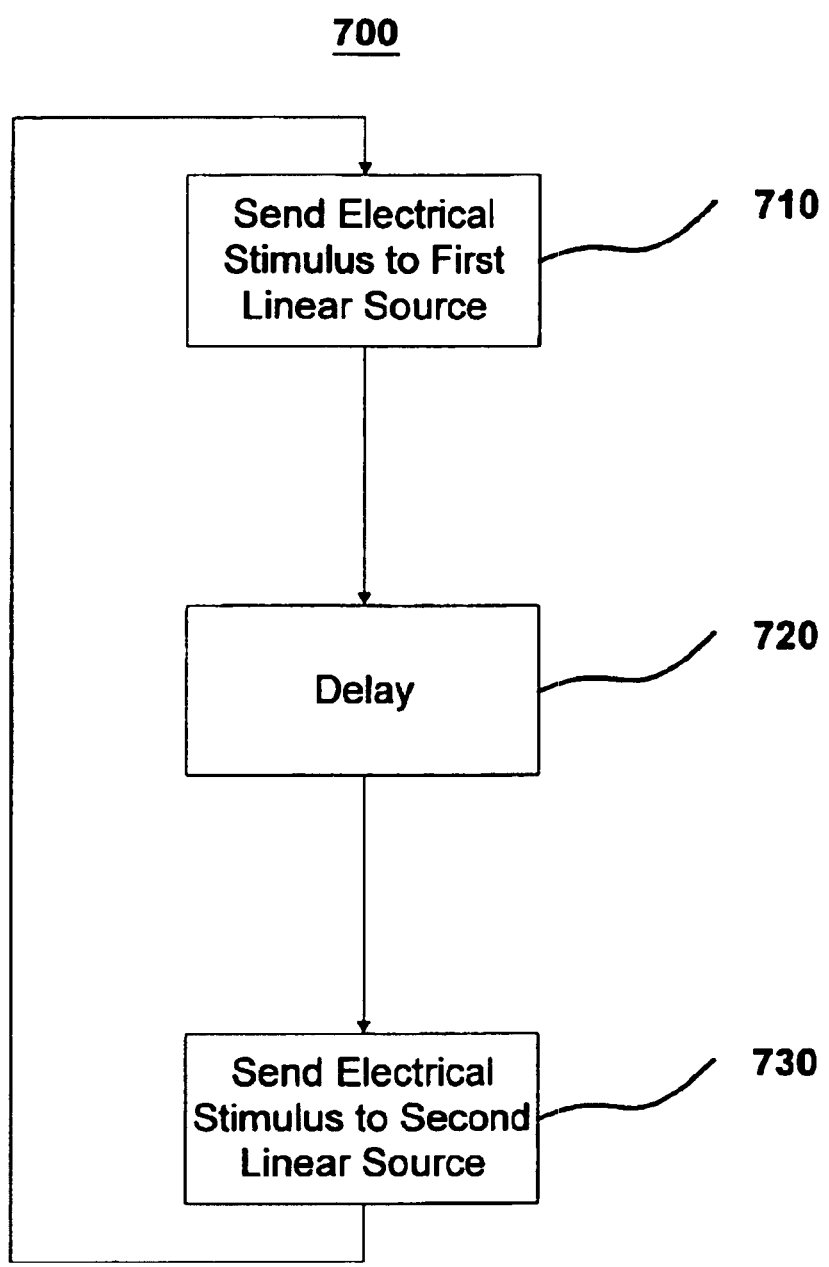
FIG. 7 depicts the operational flow of a linear source resynchronization system according to a preferred embodiment of the invention.

A methodology 700 for independent control by CRM device 601 of each linear source 605,606 is shown in FIG. 7. In module 710, a CRM device communicates a first electrical stimulus to a first linear source. Then, during module 720, the CRM device delays for a predetermined amount of time. Finally, in module 730, the CRM device sends a second electrical stimulus to a second linear source. The methodology 700 is then repeated for each contraction of the heart.

Applying this methodology 700 to the embodiment shown in FIG. 6, an electrical stimulus is initially sent to linear source 606 so as to linearly excite free wall region 636 near the apex of the heart. The CRM device 601 then delays for a predetermined time period. Finally, an electrical stimulus is sent to linear source 605 so as to linearly excite free wall region 637 near the base of the heart. In this manner, the delay in module 720 can be calculated so that linear excitation by CRM device 601 may create an apex-to-base pattern of electrical excitation similar to that in hearts with an intact His-Purkinje system.

Figure 8:
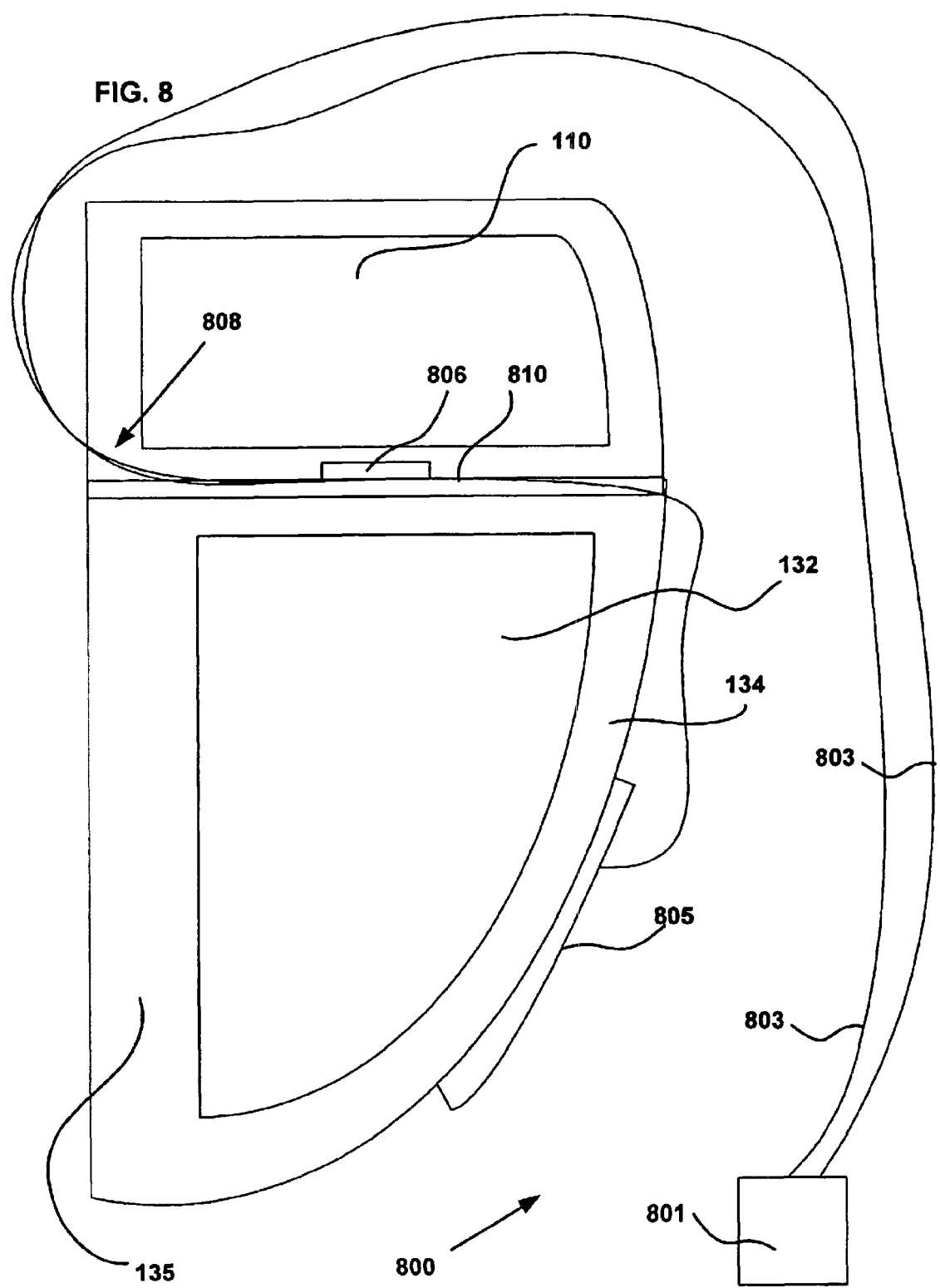
FIG. 8 shows a linear source resynchronization system according to a preferred embodiment of the invention.

Illustrated in FIG. 8 is a further preferred embodiment according to the present invention. The left ventricle 132 is shown with left ventricular free wall 134 and interventricular septum 135. The left atrium 110 is further depicted along with the coronary sinus 808 and great vein 810. The resynchronization system 800 includes CRM device 801, leads 803, linear source 805, and point source 806. The leads 803 may be disposed through the coronary sinus 808 and within the great vein 810 of the heart. The linear source 805 is positioned so as, to contact a surface of the left ventricular free wall 134, and the point source 806 is positioned within the great vein 810 so as to be electrically coupled to the left atrium 110. Resynchronization system 800 may function by sending a first electrical stimulus from CRM device 801 to the point source 806 to resynchronize contraction in the left atrium. Subsequently, a second electrical stimulus may be sent to the linear source 805 to resynchronize contraction of the left ventricle. Therefore, resynchronization system 800, positioned in this manner, may resynchronize left atrial contraction as well as left ventricle contraction.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

What is claimed is:

1. A method for resynchronization of a heart comprising the steps of:
    (a) coupling a linear source to a cardiac rhythm management device via a lead;
    (b) coupling the linear source to a surface of the heart; and
    (c) resynchronizing a contraction of the heart through linear excitation of the surface by the linear source.

2. The method of claim 1, wherein the coupling step (b) further comprises selecting a portion of left ventricular epicardium as the surface of the heart.

3. The method of claim 1, wherein the coupling step (b) further comprises selecting a portion of left ventricular free wall as the surface of the heart.

4. The method of claim 1, further comprising the steps of:
    (d) coupling a second linear source to the cardiac rhythm management device via a second lead; and
    (e) coupling the second linear source to a surface of a right ventricle of the heart.

5. The method of claim 1, further comprising the steps of:
    (d) coupling a second source to the cardiac rhythm management device via a second lead; and
    (e) coupling the second source to a surface of an atrium of the heart.

6. A method of resynchronization of a heart comprising the steps of:
    (a) coupling a first linear source to a left ventricular free wall adjacent an apex of the heart; and
    (b) sending a first electrical stimulus to the first linear source.

7. The method of claim 6, further comprising the steps of:
    (c) coupling a second linear source to the left ventricular free wall nearer a base of the heart; and
    (d) sending a second electrical stimulus to the second linear source.

8. The method of claim 7, wherein the sending step (d) further comprises pausing for a delay before sending the second electrical stimulus.

9. The method of claim 8, wherein the sending step (d) further comprises calculating the delay such that the heart is stimulated so as to approximate normal apex-to-base contraction.

* * * * *

UNITED STATES PATENT AND TRADEMARK OFFICE
CERTIFICATE OF CORRECTION

PATENT NO. : 6,829,506 B2  Page 1 of 1
APPLICATION NO. : 09/915088
DATED : December 7, 2004
INVENTOR(S) : Pastore et al.

It is certified that error appears in the above-identified patent and that said Letters Patent is hereby corrected as shown below:

Drawings, Sheet 1 of 8: FIG. 1 is the wrong drawing. Please insert the following correct drawing of FIG. 1 as shown below:

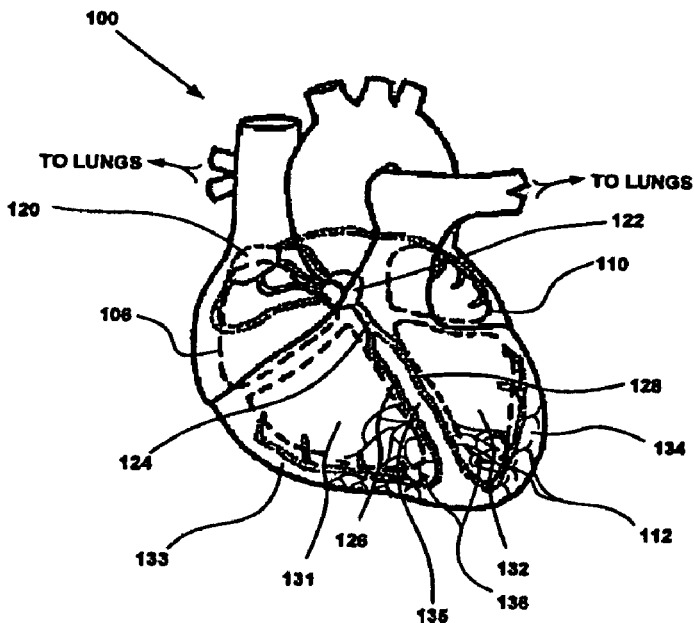

FIG. 1

Signed and Sealed this

Twenty-ninth Day of January, 2008

JON W. DUDAS
*Director of the United States Patent and Trademark Office*